United States Patent [19]

Sawai et al.

[11] Patent Number: 4,889,715

[45] Date of Patent: * Dec. 26, 1989

[54] COMPOSITION CONTAINING ORGANOGERMANIUM COMPOUND AND IMMUNITY ADJUSTING AGENT COMPRISING THE COMPOSITION

[75] Inventors: Kiichi Sawai, Funabashi; Masayasu Kurono; Juichi Awaya, both of Nagoya; Akio Kojima, Kasugai; Hideaki Ninomiya, Nagoya, all of Japan

[73] Assignee: Sanwa Kagaku Kenkyusho Co., Ltd., Aichi, Japan

[ * ] Notice: The portion of the term of this patent subsequent to Sep. 26, 2005 has been disclaimed.

[21] Appl. No.: 224,279

[22] Filed: Jul. 25, 1988

Related U.S. Application Data

[63] Continuation-in-part of Ser. No. 809, 819 Dec. 17, 1985.

[30] Foreign Application Priority Data

Dec. 25, 1984 [JP] Japan .................. 59-272057

[51] Int. Cl.$^4$ .................. A61K 31/79; A61K 31/555; A61K 31/28
[52] U.S. Cl. .................. 424/80; 514/184; 514/492
[58] Field of Search .................. 424/80; 514/184, 492

[56] References Cited

U.S. PATENT DOCUMENTS 4,229,468  10/1980  Miyao et al. .................. 514/492
4,322,402  3/1982   Ishikawa et al. .................. 514/492

FOREIGN PATENT DOCUMENTS 147932  11/1979  Japan .................. 514/492
118015   9/1981  Japan .................. 514/492
190714   9/1985  Japan .................. 514/492

OTHER PUBLICATIONS

The Merck Index, 9th Ed., Merck & Co., Inc. Rathway, N.J. 1976, p. 996 (No. 7498).

Primary Examiner—Jerome D. Goldberg
Attorney, Agent, or Firm—Armstrong, Nikaido, Marmelstein, Kubovcik & Murray

[57] ABSTRACT

A composition comprising an organogermanium compound represented by the formula

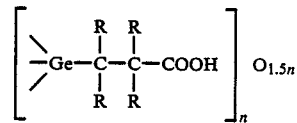

wherein n is an integer of 1 or more, R is hydrogen, alkyl, —COOH, —COOR', phenyl,

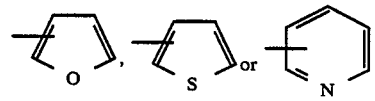

and R' is a lower alkyl
and a high molecular carrier, as well as an immunity adjusting agent comprising the composition.

2 Claims, 14 Drawing Sheets

COMPOSITION CONTAINING ORGANOGERMANIUM COMPOUND AND IMMUNITY ADJUSTING AGENT COMPRISING THE COMPOSITION

This application is a continuation of application Ser. No. 809,819 filed Dec. 17, 1985 now abandoned.

BACKGROUND OF THE INVENTION

1. Field of the Invention

The present invention relates to a composition containing an organogermanium compound and an immunity adjusting agent comprising the composition. The organogermanium compound is represented by the formula

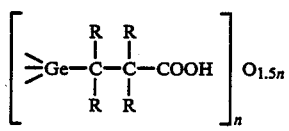

wherein n is an integer of 1 or more, R is hydrogen, alkyl, —COOH, —COOR', phenyl,

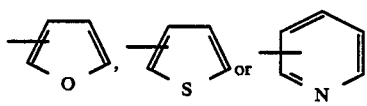

and R' is a lower alkyl.

2. Related Arts

The organogermanium compound (polymer) represented by Formula I has been watched with great interest in recent years, due to attractive pharmacological activities thereof and thus various derivatives have been synthesized.

However, these organogermanium compounds as proposed have a common disadvantage of that it is not so stable to water. Namely, when such an organogermanium compound is prepared through a hydrolysis of trichlorogermylpropionic acid, some different organogermanium compounds will be formed, as disclosed in Examined Jap. Pat. Appln. Gazette Nos. 2498/1971 and 53800/1982 as well as Unexamined Jap. Pat. Appln. Gazette No. 102895/1982. It means a fact that a product will be made different, due to a slight difference in term or condition for the hydrolysis reaction. Therefore, such a possibility is to be estimated that a certain product may change into another product, when the former will be suspended or dissolved in water and a generation of this phenomenon has actually been reported (Examined Jap. Pat. Appln. Gazette Nos. 53800/1982 and 18399/1984).

The inventors have carefully studied on pharmacological activities of the various organogermanium compounds represented by said Formula I, which have been prepared by a common process but under a different synthetic condition, to find that each compound shows a remarkable difference in degree of the pharmacological activity. Now, it is, of course, required to obtain specific organogermanium compounds which show a high and stable pharmacological activity, for utilizing same as an effective component for a pharmaceutical agent. However, it has further been confirmed by the inventors on the compounds of Formula I and more particularly those, wherein all of the substituents R in the Formula is hydrogen, that a polymerization degree varies due to a slight difference in synthetic conditions therefor, that a form as the pharmaceutical agent is limited to a solid one only, since an intermolecular bond therein is easily severed or broken due to a slight change in environment or atmosphere, and that a stable appearance of pharmacological activities inherent to the compound can not be expected, since at least partial decomposition thereof occurs prior to reach to a desired absorption area in a living body.

Hitherto, a large number of reports to the effect that the organogermanium compounds in question have an immunity accerating action as one of those pharmacological actions has been issued, but each of such compounds has not only been employed for developing a pharmaceutical agent, due to its low stability and other difficulties but also been considered as a harmful substance to various diseases or disorders concerning to an immunity acceration system.

However, the inventors have now found through their various studies that the organogermanium compounds in question show great effectivity on various immunity disorders, namely both of the immunity inhibition system disorders and the immunity acceration system disorders and thus the "immunity accerating action" which has hithereto been reported and widely been accepted is not right and should be corrected to an—immunity adjusting or regulating action—.

OBJECT AND SUMMARY OF THE INVENTION

Therefore, an object of the invention is to provide a composition, in which at least one of the compounds of Formula I is physicochemically and pharmacologically stabilized.

Another object of the invention is to provide an immunity adjusting agent useful as a therapeutic agent for various immunity disorders due to an abnormal increase or decrease of immunity function in living bodies.

According to the invention, the objects can be attained by a composition comprising an organogermanium compound represented by the formula

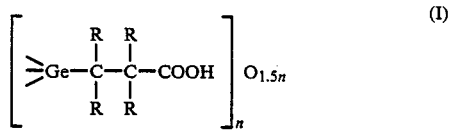

wherein R has the meaning as referred to and a high molecular carrier for pharmaceutical agents, as well as an immunity adjusting agent comprising the composition.

The organogermanium compound composed in the composition or the immunity adjusting agent according to the invention can be obtained by treating in a halogenohydroacid, germanium dioxide with hydrophosphorous acid or a salt thereof, reacting the resulting halogenogermanium-phosphoric acid complex with a compound represented by the formula

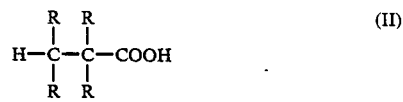

wherein R has the meaning as referred to dissolving the resulting compound represented by the formula

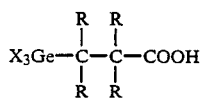

wherein R has the meaning as referred to and X is a halogen into acetone or another organic solvent having a solubility to water, and adding water into the solution.

The high molecular carrier composed in the composition or the immunity adjusting agent according to the invention serves also to stabilize the organogermanium compound as the main component and a natural high molecular substance, synthetic high molecular substance, proteinic substance or saccharoid may be employed therefor. It is preferable to compose the carrier in an amount ranging from 0.01 to 200 parts by weight, for instance 0.05 to 5 parts by weight based on 1 weight part of the organogermanium compound. As the natural high molecular substance, biological one, for instance gelatin, pepsin, serum albumin (cattle, horse or human origin), globulin, protamine and a mixture thereof may be listed. As the synthetic high molecular weight substance, polyethylene glycol and the like glycols; hydroxypropylcellulose, hydroxypropylmethylcellulose and the like cellulosic high molecular substances, polyvinylpyrrolidone and the like vinylic high molecular substances; and polyacryloamide and the like acrylic high molecular substances may be listed. As the proteinic high molecular substance, in general, additives for culture mediums, for instance peptone, polypeptone, yeast extract, tryptone, tryptose, dextrose and the like may be listed. As the saccharoid, lactose, refined sugar, glucose, starch, cellulose and the like may be listed.

The compounds as shown in following Table 1 may be listed as exemplary organogermanium compounds to be employed for the invention.

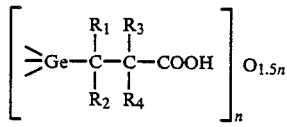

TABLE 1

| Compound number | $R_1$ | $R_2$ | $R_3$ | $R_4$ | Crystal form and dec. temperature |
|---|---|---|---|---|---|
| 1 | H | H | H | H | white needle, 240° C. |
| 2 | $CH_3$ | H | H | H | white crystal, more than 300° C. |
| 3 | $C_2H_5$ | H | H | H | white crystal, more than 300° C. |
| 4 | $(CH_2)_2CH_3$ | H | H | H | white crystal, more than 300° C. |
| 5 | $(CH_2)_4CH_3$ | H | H | H | white crystal, more than 300° C. |
| 6 | $(CH_2)_{12}CH_3$ | H | H | H | white crystal, 172-176° C. |
| 7 | H | H | $CH_3$ | H | white needle, more than 300° C. |
| 8 | H | H | $C_2H_5$ | H | white crystal, more than 300° C. |
| 9 | $CH_3$ | H | $CH_3$ | H | white crystal, more than 300° C. |
| 10 | $CH_3$ | $CH_3$ | H | H | white crystal, more than 300° C. |
| 11 | COOH | H | H | H | white crystal, more than 300° C. |

TABLE 1-continued

| Compound number | $R_1$ | $R_2$ | $R_3$ | $R_4$ | Crystal form and dec. temperature |
|---|---|---|---|---|---|
| 12 | $C_6H_5$ | H | H | H | white crystal, more than 300° C. |

For making the composition into a pharmaceutical agent, a filling, binder, disintegrator and the like aids may be composed, but such aid should be one showing no reactivity to the organogermanium compound as the main component and no activity to a delayed type immunity response reaction test, from a pharmacological view point.

A dosing form as the pharmaceutical agent may freely be selected to make the composition into a solid one, for instance a tablet, capsule, granule, infinitesimal grain, powder, suppository, dry syrup or the like; a solution one, for instance an injection, orally dosing solution agent, external lotion or the like; or a semi-solid one, for instance an externally applying cream, jelly or the like.

It is preferable to dose the human in an amount of 0.3 to 20 mg/kg, for instance 1 mg/kg, as an amount of the organogermanium compound.

EFFECT OR ADVANTAGE OF THE INVENTION

According to the invention, the organogermanium compound as the main component is effectively stabilized to allow free selection in dosing form thereof as the pharmaceutical agent, so that pharmacological activities of the organogermanium compound can sufficiently be utilized.

The immunity adjusting agent of the invention shows a powerful and stable physiological activity through an immunity system and is useful as a curing agent for various self immunity disorders such as a viral disease, phlegmasia, hepatopathy, nephropathy, collagenosis and the like as well as a inhibition agent to a negative reaction possibly caused in an organ implanting.

BRIEF DESCRIPTION OF THE DRAWINGS

FIGS. 1-7 are graphs showing IR spectrums measured on an organogermanium compound as employed for the present invention, in which FIG. 1 is one on an original or non-treated compound, FIG. 2 is one on a composition of the original compound and a serum albumin, which has lapsed 30 days.

FIG. 3 is one on a composition of the original compound and hydroxypropylcellulose, which has lapsed 30 days, FIG. 4 is one on a composition of the original compound and γ-globulin, which has lapsed 30 days, FIG. 5 is one on a composition of the original compound and pepsin, which has lapsed 30 days, FIGS. 6 and 7 are one on 4% aqueous solution of the original compound, which has lapsed 24 and 60 hours, respectively;

DETAILED DESCRIPTION OF PREFERRED EMBODIMENTS

The invention will now be explained with reference to stability test examples, pharmacological test examples and pharmaceutical agent preparation examples.

Stability Tests (1) Physico-chemical stability test (a) To 5 ml of 4% cattle serum albumin solution, 200 mg of the organogermanium compound (Compound No. 1 in said Table 1) were added and dispersed therein by a mixer to prepare a composition of the invention (4% suspension of the organogermanium compound).

The suspension was stored in a thermostat kept at 25° C., sampled out after lapsed 1, 3, 9, 15 and 30 days and filtered. Each resulting solid substance was washed with acetone and ethanol and then dried for 1 hour at 105° C.

As to the resulting dried substance, a stability thereof was checked by measuring an IR spectrum, in accordance with potassium bromide tablet method.

Figure 1:
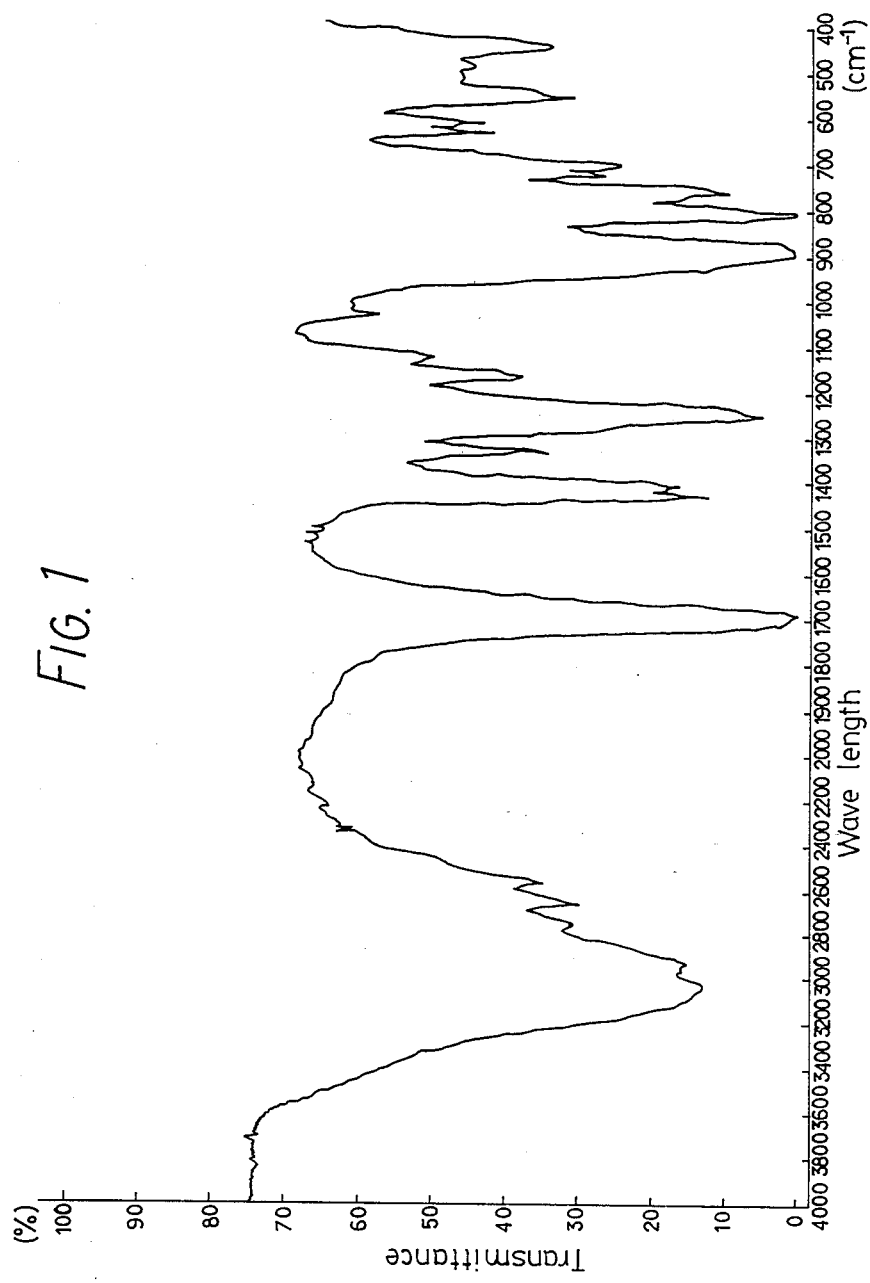

An IR spectrum of the original or non-treated organogermanium compound is shown in FIG. 1 and has characteristic absorption spectrum at 1695, 1435, 1255, 890 and 805 cm, and thus a stability in question was judged on the basis of such chracteristic absorption spectrum.

Figure 2:
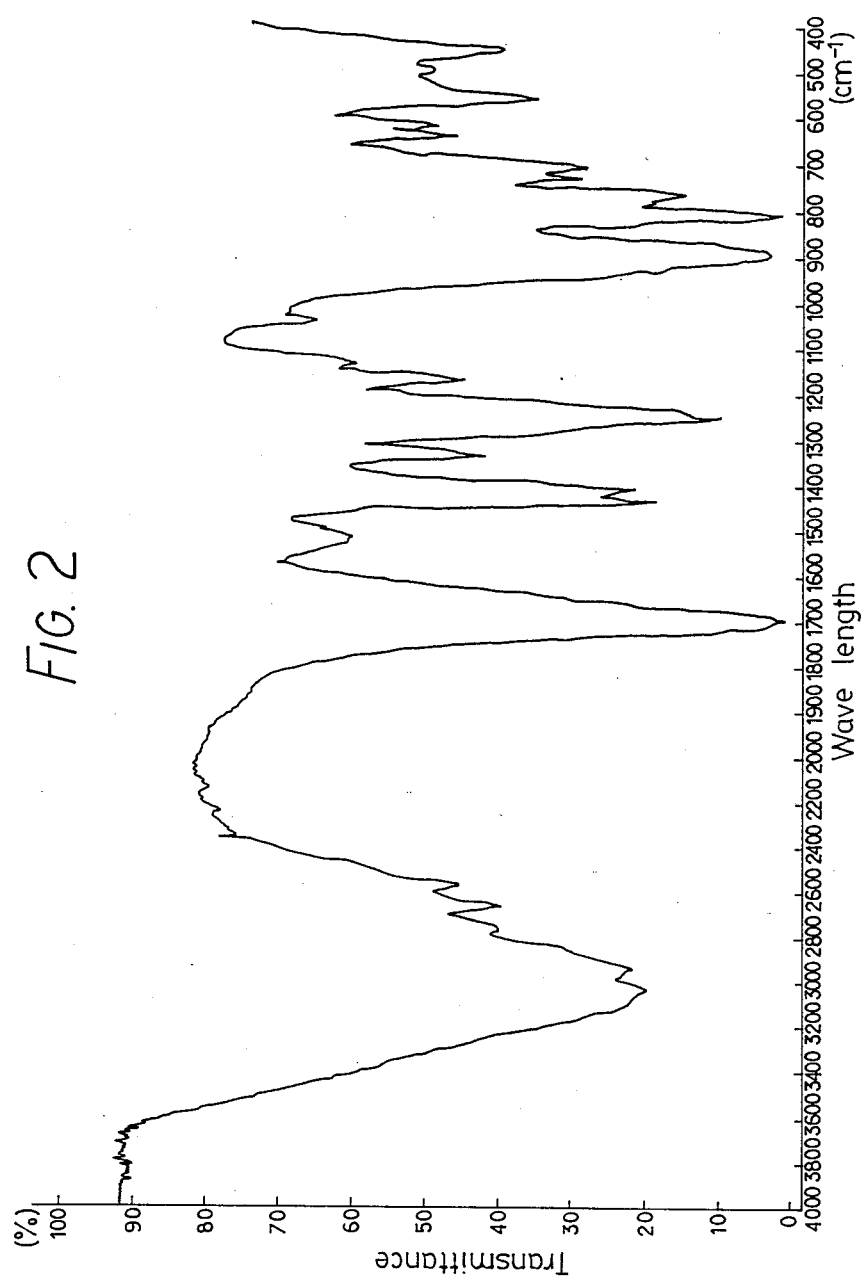

The tested composition was kept in stable state, even when it has been lapsed for 30 days (see FIG. 2).

Figure 6:
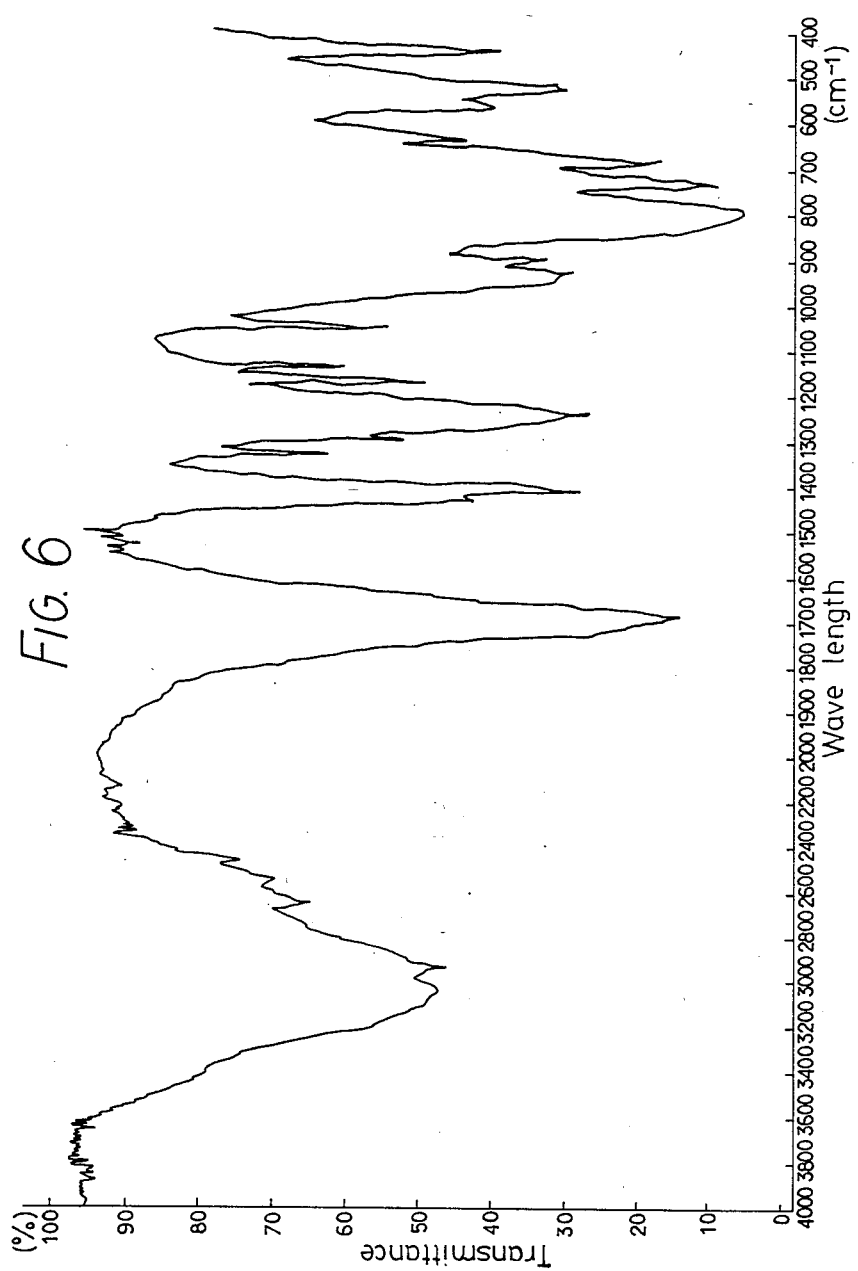
Figure 7:
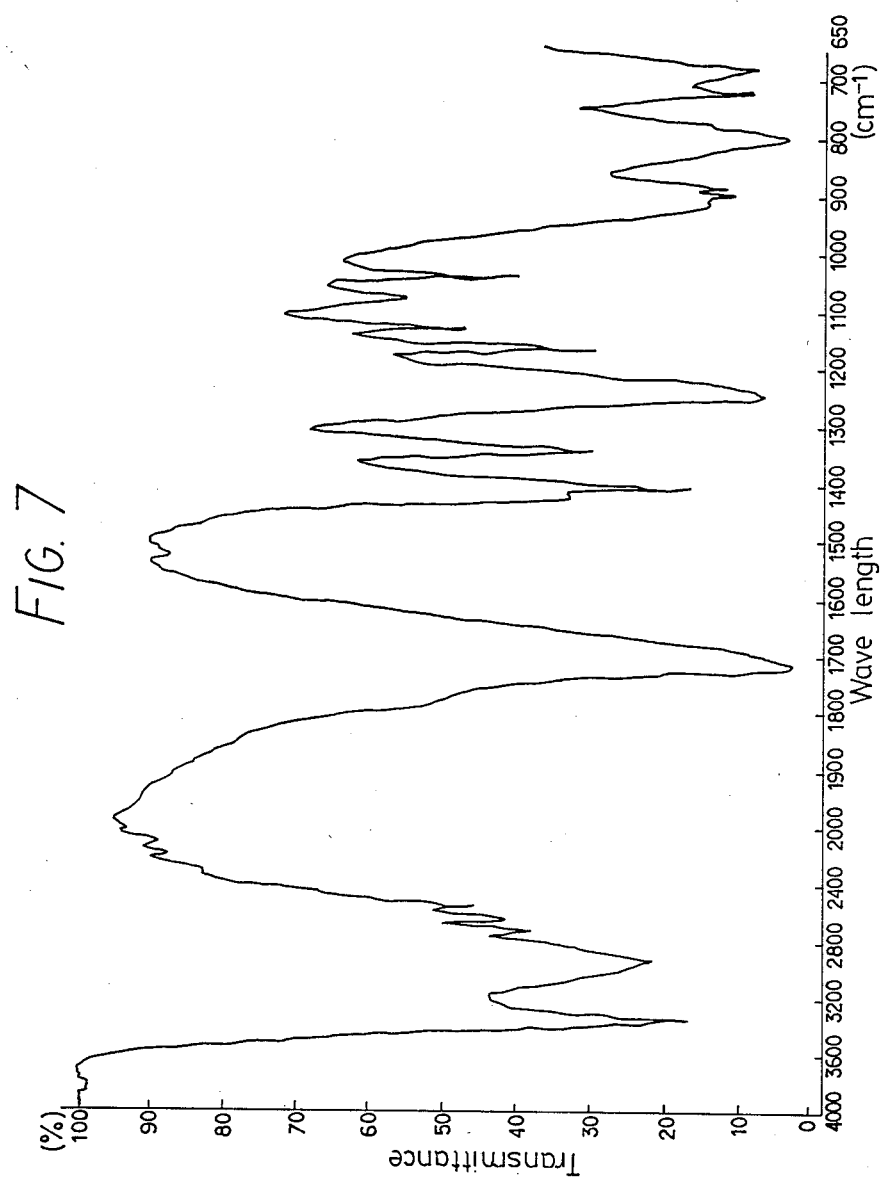

As as control, a composition was prepared with use of water in lieu of the serum albumin and its stability was measured in a manner similar to the above to find that a disturbance in the absorption spectrum was first observed on the sample having lapsed for 24 hours (see FIG. 6) and that the disturbance was further increased on the sample lapsed for 60 hours (see FIG. 7). This shows a fact that a modification or decomposition occurs in the organogermanium compound in control composition.

Figure 3:
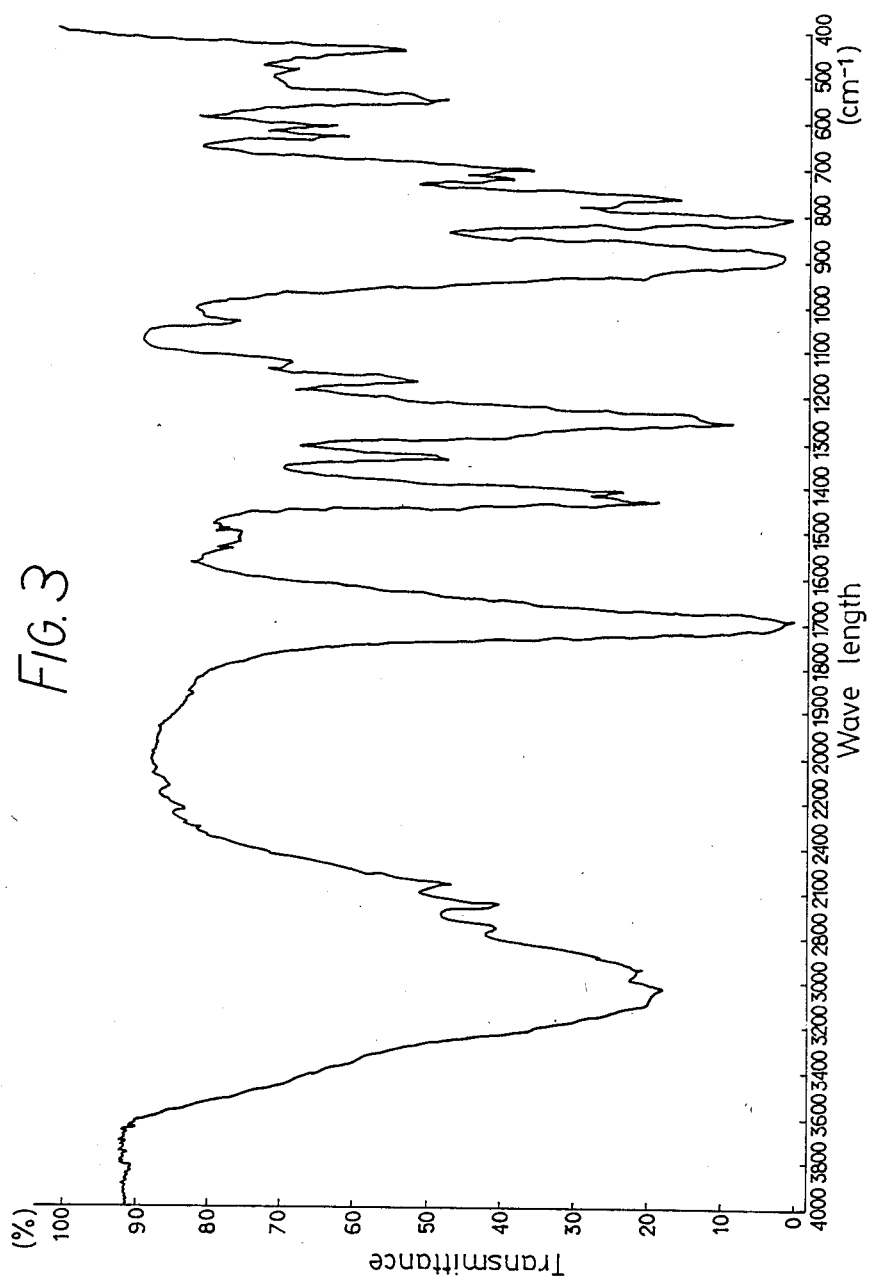
Figure 4:
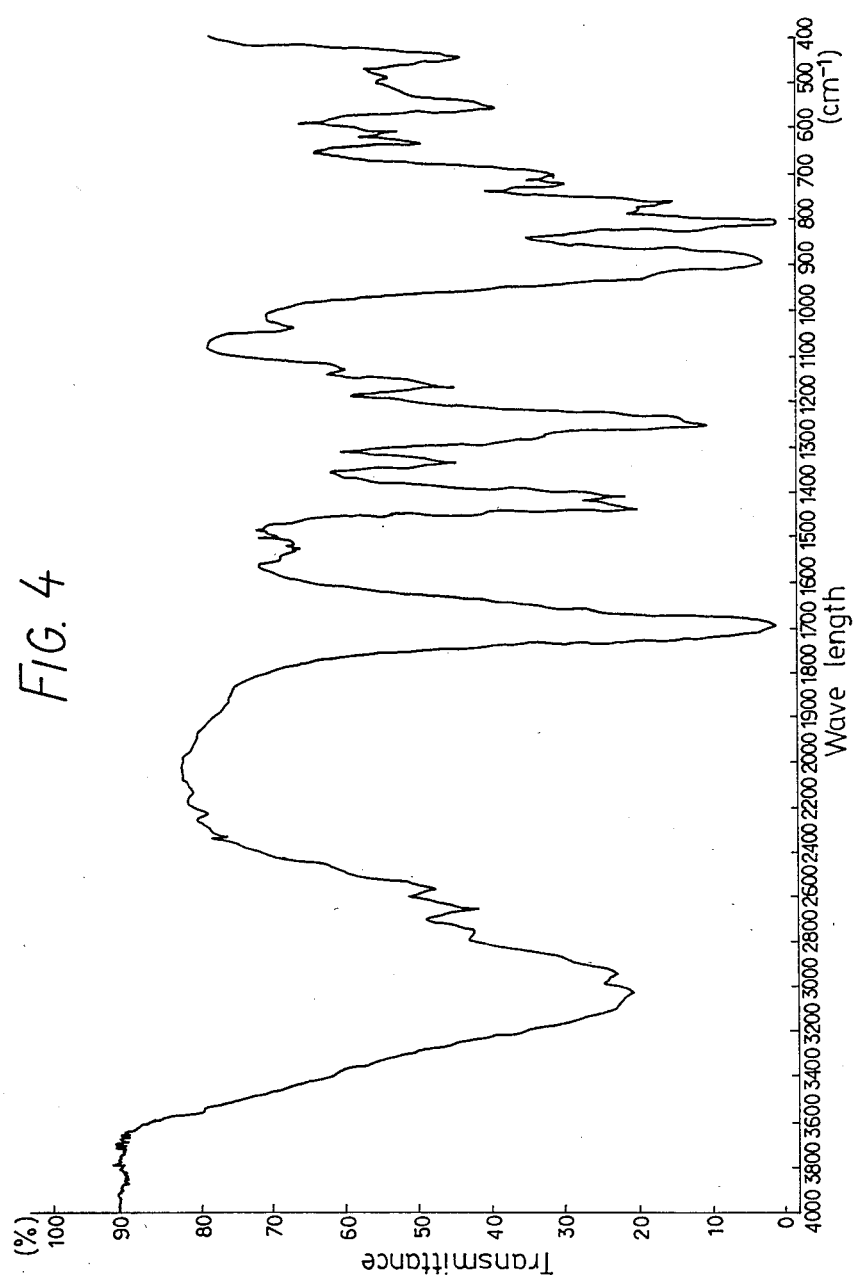
Figure 5:
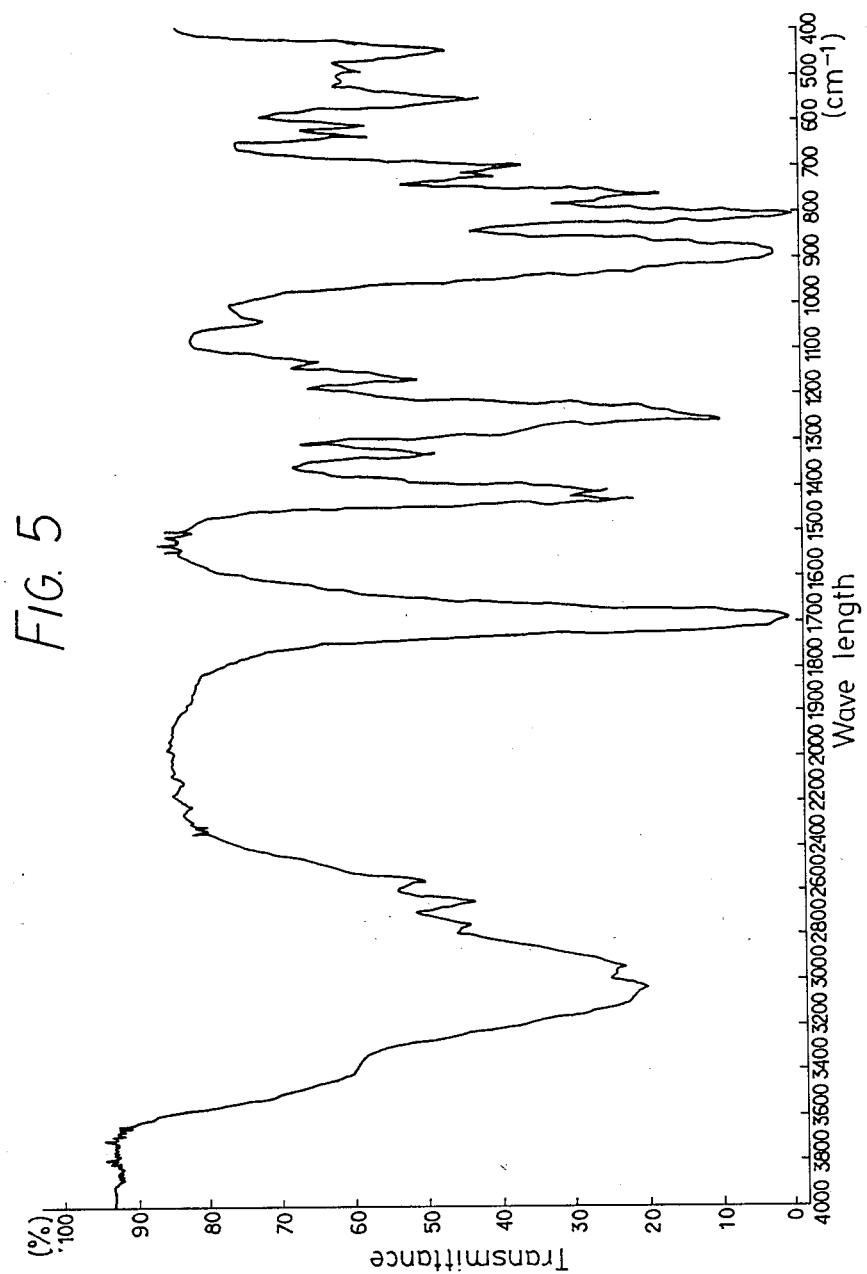

(b) Compositions according to the invention were prepared as in the case of said Item a but with use of hydroxypropylcellulose, γ-globulin and pepsin, respectively, in lieu of the serum albumin. Each of the compositions was tested as in the case of said Item a to find that the organogermanium compound is kept in stable state, by virtue of coexsistence with such a high molecular carrier (see FIGS. 3 to 5).

A similar result was obtained on various compositions, wherein geratin, protamine, hydroxypropylmethylcellulose, polyvinylpyrrolidone, polyacryloamide, peptone, polypeptone, yeast extract, trypton, tryptose, dextrose, lactose, refined sugar, glucose, starch or cellulose was employed as the high molecular carrier for the organogermanium compound, in lieu of the serum albumin.

2. Biological stability test

Effect to delayed type hyperergy (DTH) on cancered mouse: After implantation of $10^6$ cells of sarcoma 180 cancer cell in an abdominal canal of ICR mice, $10^6$ corpuscles of sheep red blood corpuscle (SRBC) were venously injected for sensitization. After lapsed 4 days from the implantation, $2 \times 10^8$ cells of SRBC were injectionally dosed at a heel of a hind leg of said mice to cause the DTH. After 24 hours from the dosage, a degree of swelling was checked by measuring a thickness of the heel.

On the other hand, various testing compositions (Nos. 1 to 10 in following Table 2) were prepared with use of various high molecular carrier and adding the organogermanium compound (Compound No. 1 in said Table 1), so as to make its concentration of 1 mg/10 ml, and a control testing composition was prepared by adding the organogermanium compound in water to make its concentration of 1 mg/10 ml. Each of the compositions was orally dosed to each mouse, respectively before 4 days of the cancer cell (Sarcoma 180) implantation and in an amount of 1 mg/10ml/kg.

Results are shown in the following Table 2. From the Table, it can be seen that each of the compositions according to the invention increases the DTH of the cancered mouse but the control composition is not effective in the dosing amount of 1 mg/kg.

TABLE 2

|  | heel swelling (× 0.01 mm) mean value ± standard deviation value |
|---|---|
| Non-treated | 114.1 ± 11.5 |
| Cancered | 57.2 ± 7.6 |
| Control composition | 57.0 ± 6.3 |
| Composition of the invention |  |
| No. 1 (5% cattle serum albumin) | 75.3 ± 6.3 |
| No. 2 (0.5% gelatin) | 99.9 ± 7.3 |
| No. 3 (1% pepsin) | 109.5 ± 9.2 |
| No. 4 (cattle fetal serum) | 100.8 ± 8.4 |
| No. 5 (10% horse serum albumin) | 96.15 ± 5.6 |
| No. 6 (0.5% polyethylene glycol) | 105.2 ± 8.2 |
| No. 7 (0.5% hydroxypropylcellulose) | 98.3 ± 5.8 |
| No. 8 (0.5% polyvinylpyrrolidone) | 108.3 ± 2.1 |
| No. 9 (0.5% polyacryloamide) | 113.1 ± 2.8 |
| No. 10 (1% peptone) | 92.6 ± 5.4 |

PHARMACOLOGICAL TEST EXAMPLE 1

(Influence of Organogermanium Compound on Antibody Production Ability in Normal Mouse)

(a) Object

An effect of the organogermanium compound (Compound No. 1 in said Table 1) is checked by sensitizing mice with an antibody in an amount of generating a sufficient antigen excitement to develop an immunity response in maximum level or not developing a sufficient immunity response due to no sufficient antigen excitement.

(b) Operation

To each group of ICR mice (age, 5 weeks), $2 \times 10^8$ and $2 \times 10^7$ corpuscles of sheep red blood corpuscle (SRBC) as an antibody were venously injected for sensitization in a tail vein of the mice. Then, immediately, the organogermanium compound dissolved in 4% cattle serum albumin solution was orally dosed to the sensitized mice in an amount of 0.1, 1.0 and 10 mg/kg, respectively. After 4 days from the sensitization, spleen cells were extracted to measure a number of PFC therein, which was made as an index of the antibody productivity.

(c) Results and consideration

Figure 8A:
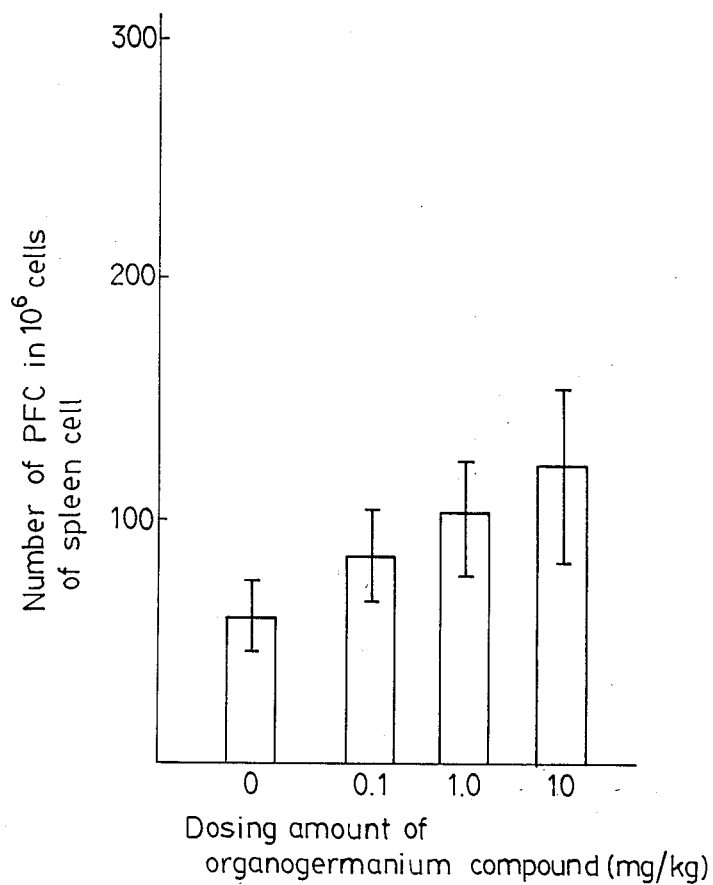
FIGS. 8a and 8b are graphs showing an influence of the compound on an antibody production ability, when normal mice are sensitized with SRBC of $2 \times 10^8$ and $2 \times 10^7$, respectively.
Figure 8B:
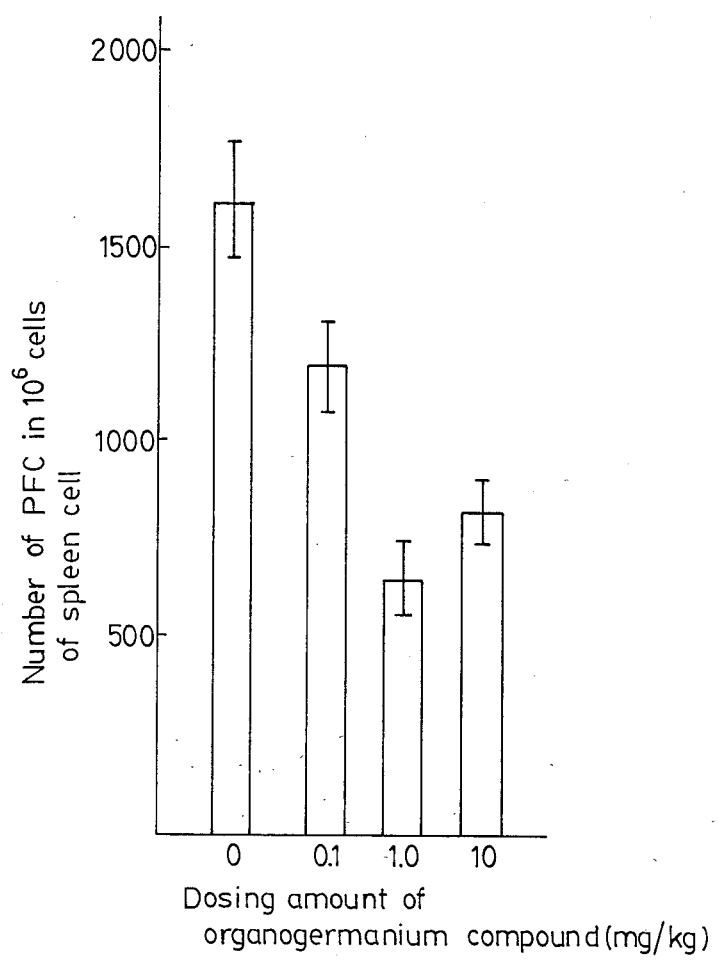

Results in the experimental group sensitized with $2 \times 10^8$ corpuscles of SRBC and the other group sensitized with $2\times10^7$ corpuscles of SRBC are shown in FIGS. 8a and 8b, respectively. From the figures, such a tendency can be seen that a spleen cell PFC is decreased, in the former group but is increased in the latter group.

These facts apparently show that the organogermanium compound reveals an immunity adjusting action.

PHARMACOLOGICAL TEST EXAMPLE 2

(Influence of Organogermanium Compound on Antibody Production Ability in Cancered Mouse)

(a) Object

Similar to the object as referred to in the Pharmacological Test Example 1.

(b) Operation $2\times10^6$ cells of a mouse tumor cell (Sarcoma 180) were implanted under a skin of a side part of ICR male mice to form a solid cancer. The organogermanium compound (Compound No. 1 in said Table 1) dissolved in 4% cattle serum albumin solution was orally dosed to the cancered mice for 5 days after lapsed 9 days from the implantation, $2\times10^8$ corpuscles of SRBC were injected in a tail vein of the mice for sensitization. After 4 days from the sensitization, spleen cells were extracted to measure of PFC therein, which was made as an index of the antibody productivity.

(c) Results and consideration

Figure 9:
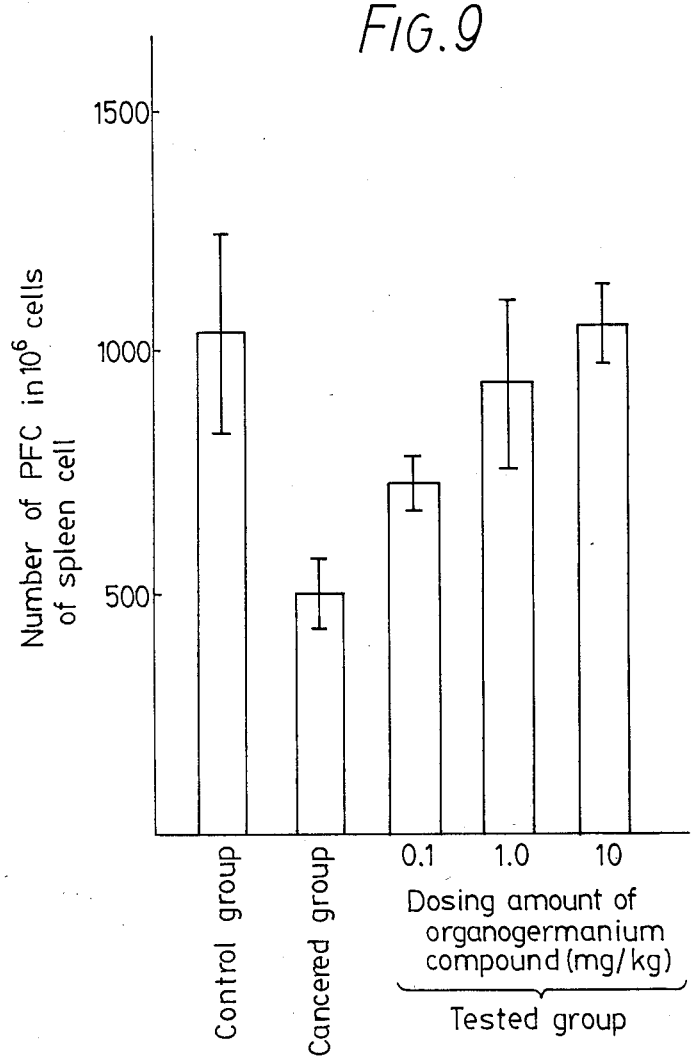
FIG. 9 is a graph showing an influence of the compound on an antibody production ability in cancered mice.

Results are shown in FIG. 9. As seen from the figure, it has been found that the antibody production ability reduces due to generation of the cancer, but by dosing the organogermanium compound, the antibody production ability will become recovered towards a normal level, depending on a dosing amount of the compound.

By taking this result and the result as shown in FIG. 8a into consideration, it is apparent that the organogermanium compound develops an immunity adjusting action.

PHARMACOLOGICAL TEST EXAMPLE 3

(Influence of the Organogermanium Compound on Antibody Production Ability in Culture System for Mouse Lymphocyte)

(a) Object

Influence of the organogermanium compound (Compound No. 1 in said Table 1) on SRBC is checked on a culture system of lymphocytes extracted from NZB/W $F_1$ mice who generates a self immunity disease due to a functional reduction of suppresser T cells as well as normal BALB/C mice.

(b) Operation

Spleen lymphocytes were extracted from NZB/W $F_1$ male mice (age, 14–15 weeks) and BALB/C male mice (age, 10–13 weeks), washed with a Hanks solution, dispersed the lymphocytes through a 100 mesh filter and then washed twice with the Hanks solution. The resulting lymphocytes were dispersed in a 10% cattle fatal serum added BPMI 1640 culture medium (including 2-mercaptoethanol in $5\times10^5$M) and containing the organo-germanium compound and a lymphocyte concentration of the dispersion was regulated with a Turk solution into $1.2\times10^7$ corpuscles/ml.

On the other hand, SRBC was washed twice with the Hanks solution and then dispersed in a manner similar to the above into the 10% cattle fetal serum added RPMI culture medium containing the organo-germanium compound, and a concentration of the SRBR was regulated into $1.2\times10^7$ corpuscles/ml.

Each 0.5 ml of said lymphocyte suspended medium and said SRBC suspended medium was sampled out and mixed. The mixture was charged in a microplate and cultivated for 4 to 5 days at 37° C. under 5% $CO_2$ condition. Thereafter, an anti SRBC antibody produced cell number was measured with a slide method, as a plaque forming cell number.

(c) Results and consideration

Figure 10A:
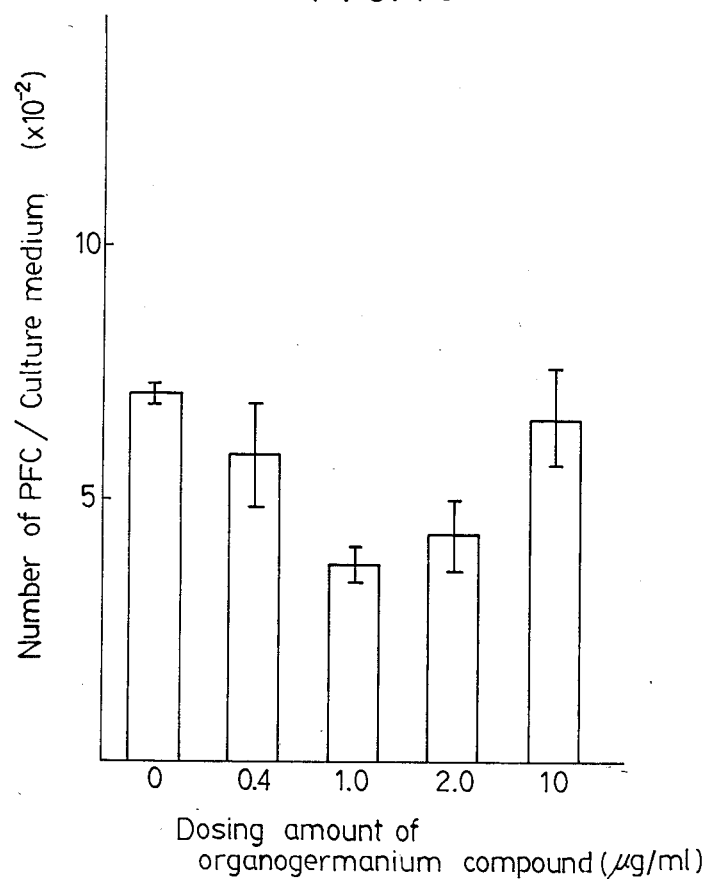
FIGS. 10a and 10b are graphs showing an influence of the compound on an antibody production ability in NZB/W F₁ mice and BALB/C mice, respectively.
Figure 10B:
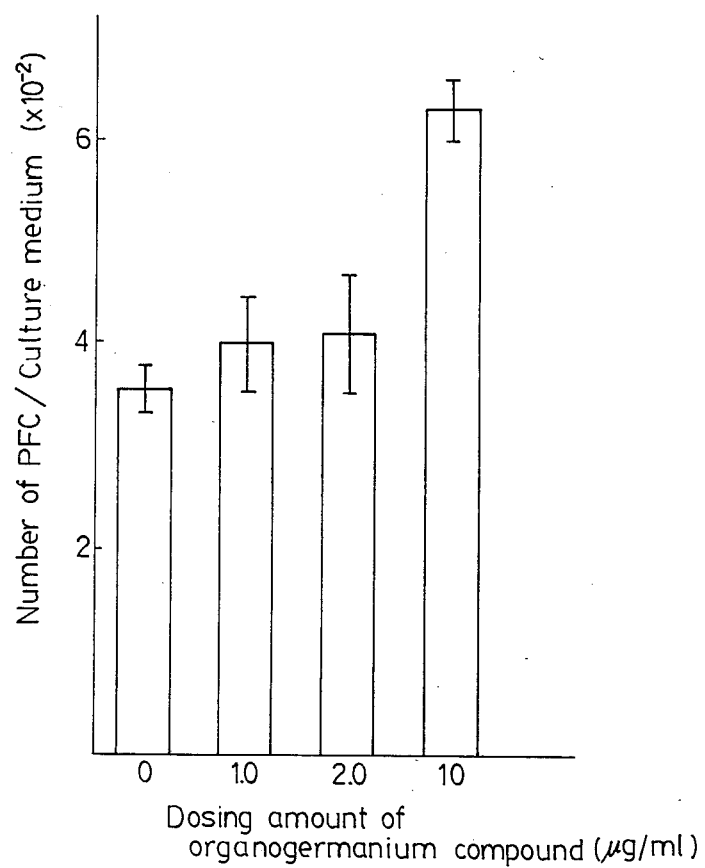

Results are shown in FIGS. 10a and 10b. From the figures, an inhibition in antibody production ability is recognized on the NZB/W $F_1$ mouse lymphocytes, when the organogermanium compound is added in the amount of 1 to 2 μg/ml (FIG. 10a) but on the BALB/C mouse lymphocytes, no change can be recognized in antibody producing function by adding the organogermanium compound in such amount and on contrary thereto, an accelation of the function can be seen, when the compound is added in the amount of 10 μg/ml (FIG. 10b).

These results also show apparently that a pharmacological action of the organogermanium compound to the immunity system is immunity adjusting one.

PHARMACOLOGICAL TEST EXAMPLE 4

(Action of Organogermanium Compound to Positive Arthus Reaction in Guinea Pig)

(a) Object

For studying a usability of the organogermanium compound (Compound No. 1 in said Table 1) to an allergic parietitis, an action thereof to an active Arthus reaction in guinea pig is checked.

(b) Operation

To 2% egg albumin solution, a same amount of Freund's complete adjuvant was added to prepare an emulsion. The emulsion was injected in 4 times by one time/week to Hartley male guinea pigs at a heel, under a skin and in femoralis muscle, for sensitization. After 10 days from the final sensitization, 0.1 ml of 1% egg albumin solution was injected under a skin of the back to measure an area of resulting edema. The organogermanium compound was orally dosed for 30 days from the first sensitization in an amount of 0.1, 1.0 and 10 mg/kg/day.

(c) Results

Figure 11:
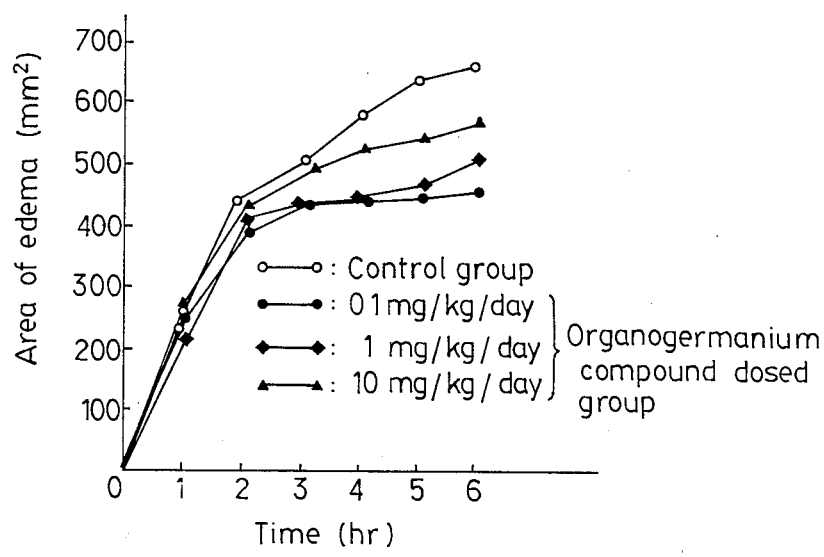
FIG. 11 is a graph showing an influence of the compound on positive Arthus reaction in guinea pigs.

Each change in the edema area is shown in FIG. 11. From the figure, a recognizable inhibition of the phlegmasia can be found in the groups, to which the organogermanium compound was dosed in a ratio of 0.1 and 1 mg/kg/day, respectively.

PHARMACOLOGICAL TEST EXAMPLE 5

(Action of Organogermanium Compound to Adjuvant Arthritis)

(a) Object

An effect of the organogermanium compound (Compound No. 1 in said Table 1) to a prevention of an adjuvant arthritis is checked.

(b) Operation 0.05 ml of an adjuvant (prepared by suspending 0.6 mg of micobacteriumbutircum into 0.05 ml of liquid paraffin) was injected under a skin of hind leg heel in S.D. male rats. After 1, 3, 5, 7, 21, and 28 days from the adjuvant dosage, a volume of the dosed and none-dosed legs was measured to determine a ratio of the edema.

The organogermanium compound was orally dosed for 28 days from the adjuvant dosage, in an amount of 1, 10 and 100 mg/kg/day, respectively.

(c) Results and consideration

Figure 12:
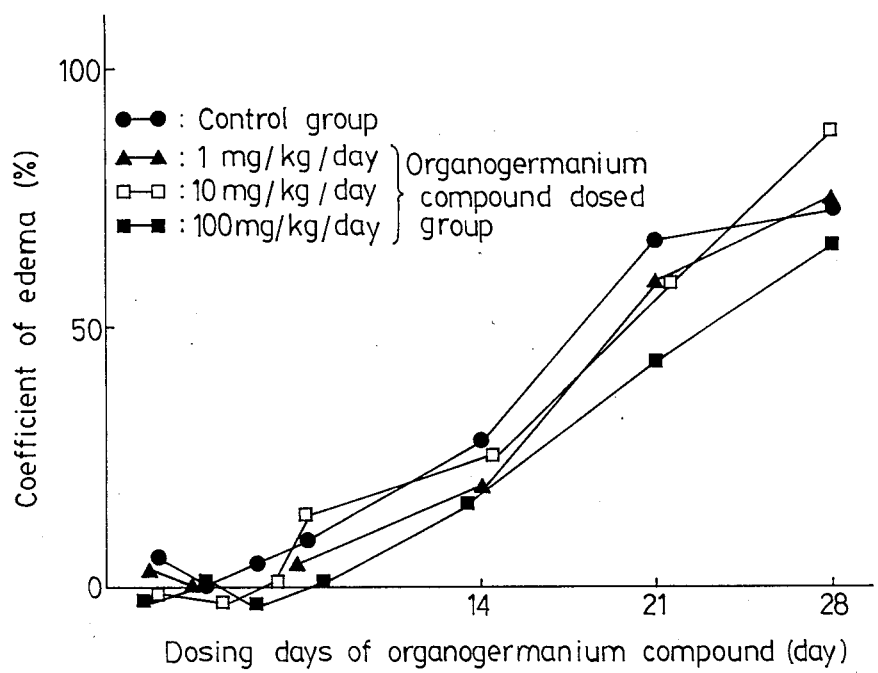
FIG. 12 is a graph showing an influence of the compound on adjuvant arthritis in rats.

Results are shown in FIG. 12. From the figure, an inhibition effect to a secondary phlegmasia after 14 to 28 days can be recognized in the group, to which the organogermanium compound was dosed in the amount of 100 mg/kg/day.

PHARMACEUTICAL AGENT PREPARATION EXAMPLE 1

(Injection)

To 0.1% solution of sodium carboxymethylcellulose, the organogermanium compound (Compound No. 1 in Table 1) was added to make a concentration of the organogermanium compound to 1.5% and then mannite was added and dissolved, so that a concentration of the mannite was made into 2%. The resulting solution was sterilized by filtration method and filled into each vial by 2 ml, and freeze dried to prepare a powder for preparing an injection.

The powder can be dissolved into isonic sodium chloride before use.

PHARMACEUTICAL AGENT PREPARATION EXAMPLE 2

(Lotion for External Application)

The organogermanium compound (Compound No. 1 in Table 1) was added into 0.5% solution of polyvinylpyrrolidone and dissolved therein to make a concentration of the organogermanium compound to 0.1%.

This solution can direcly be applied on skin or mucosa for a therapeutic purpose.

PHARMACEUTICAL AGENT PREPARATION EXAMPLE 3

(Cream for External Application)

The organogermanium compound (Compound No. 1 in Table 1) was added into 4% solution of bovine serum albumin and dissolved therein to make a concentration of the organogermanium compound to 1.0%, and then the solution was freeze dried. This freezed dry powder composition was mixed with excipients in a following prescription to prepare a cream agent (ointment).

| | |
|---|---|
| the powder composition | 0.5 (g) |
| diethyl sebacate | 8.0 |
| spermaceti | 5.0 |
| sodium polyoxyethyleneoleyletherphosphate | 6.0 |
| sodium benzoate | 0.5 |
| petrolatum | a sufficient quantity |
| Total | 100 (g) |

PHARMACEUTICAL AGENT PREPARATION EXAMPLE 4

(Suppository)

The freezed dry composition in Pharmaceutical Agent Preparation Example 3 was dispersed in melted higher fatty acid glycerides in following amount ratio and suppositories were directed from the dispersion, in a conventional method.

| | |
|---|---|
| The powder composition | 60 (mg) |
| fatty base (cacao butter) | 1640 |
| | 1700 (mg)/piece |

PHARMACEUTICAL AGENT PREPARATION EXAMPLE 5

(Tablet)

The organogermanium compound (Compound No. 1 in said Table 1) was added and dissolved in 1% aqueous solution of pepsin, to make a concentration of the organogermanium compound to 1% and then the solution was freeze dried.

The freezed dry composition was mixed with excipients in a following prescription to prepare tablets in a conventional method.

| | |
|---|---|
| The powder composition | 60 (mg) |
| lactose | 90 |
| calcium carboxymethylcellulose | 7 |
| light anhydrous silicic acid | 1 |
| magnesium stearate | 7 |
| | 165 (mg)/tablet |

PHARMACEUTICAL AGENT PREPARATION EXAMPLE 6

(Capsule)

The freezed dry composition in the Pharmaceutical Agent Preparation Example 5 was mixed with other ingredients in a following prescription and this mixture was filled into each hard gelatin capsule, in a conventional method to prepare capsuled agent.

| | |
|---|---|
| The powdered composition | 30 (mg) |
| lactose | 107 |
| hydroxypropylmethylcellulose | 2 |
| magnesium stearate | 1 |
| | 140 (mg)/capsule |

UTILIZATION EXAMPLE

The external cream agent obtained by the Pharmaceutical agent Preparation Example 3 was given to 20 volunteers who have a red swelling due to a sticking by an insect, food allergy, pain or itching due to a pile or the like local disease to use the same, when it demands. After having lapsed a certain time period, an opinionaire research was carried out to obtain results as shown in following Table 3. As seen from the Table, almost all persons answered to the effect that the cream agent has a curing effect.

TABLE 3

| | Item | | | |
|---|---|---|---|---|
| | Improved | Getting improve | Indefinite | Getting worse |
| pain or itching | 1 | 15 | 3 | 1 |
| red swelling | 11 | 3 | 5 | 1 |

We claim:

1. A stabilized 3-oxygermylpropionic acid polymer composition, which comprises 0.01 to 1 weight % of 3-oxygermylpropionic acid polymer of the formula $$[GeCH_2CH_2COOH]_nO_{1.5n}$$

wherein n is an integer of 1 or more and 0.5 to 10 weight % of a high molecular weight substance as a stabilizer for the polymer and selected from the group consisting of serum, serum albumin, pepsin and polyvinylpyrrolidone.

2. A pharmaceutical composition for relieveing itching due to immuno diseases, which comprises an effective amount of a stabilized 3-oxygermylpropionic acid polymer composition comrpising 0.01 to 1 weight % of 3-oxygermylpropionic acid polymer of the formula $$[GeCH_2CH_2COOH]_nO_{1.5n}$$

wherein n is an integer of 1 or more, and 0.5 to 10 weight % of a high molecular weight substance as a stabilizer for the polymer and selected from the group consisting of serum, serum albumin, pepsin and polyvinylpyrrolidone, and a pharmaceutically acceptable carrier.

* * * * *

UNITED STATES PATENT AND TRADEMARK OFFICE
CERTIFICATE OF CORRECTION

PATENT NO. : 4,889,715
DATED : December 26, 1989
INVENTOR(S) : SAWAI et al

It is certified that error appears in the above-identified patent and that said Letters Patent is hereby corrected as shown below:

On the cover page, Item [75], after "Ninomiya, Nagoya" add the following: --; Yoshiro Ishiwata, Nagoya; Masahiro Nakajima, Gifu--.

Signed and Sealed this

Twenty-sixth Day of March, 1991

Attest:

HARRY F. MANBECK, JR.

Attesting Officer

Commissioner of Patents and Trademarks